United States Patent [19]

Shibasaki

[11] 4,187,718
[45] Feb. 12, 1980

[54] METHOD AND APPARATUS FOR INSPECTING AN INTERNAL PRESSURE OF HERMETICALLY SEALED CONTAINER

[75] Inventor: Kyuichi Shibasaki, Yokosuka, Japan

[73] Assignee: Toyo Seikan Kaisha, Ltd., Tokyo, Japan

[21] Appl. No.: 886,010

[22] Filed: Mar. 13, 1978

[30] Foreign Application Priority Data

Mar. 26, 1977 [JP] Japan .................................. 52-32820
Dec. 5, 1977 [JP] Japan ................................ 52-145169

[51] Int. Cl.² .......................................... G01N 29/00
[52] U.S. Cl. ...................................... 73/52; 364/558
[58] Field of Search ..................... 73/52, 579, 659; 364/558

[56] References Cited

U.S. PATENT DOCUMENTS 3,596,502   8/1971   Forry et al. .............................. 73/52
3,802,252   4/1974   Hayward et al. ........................ 73/52

*Primary Examiner*—Jerry W. Myracle
*Attorney, Agent, or Firm*—Frank J. Jordan

[57] ABSTRACT

A method and apparatus for inspecting the internal pressure of hermetically sealed containers wherein a sound wave of free damped oscillation exicted at the elastic wall of a hermetically sealed container is converted and detected as an electrical signal, analysis is performed for natural self-correlation function of this detected signal by using logical operation circuits, and thus, the adequacy of the internal pressure is discriminated by measuring the period of such function.

21 Claims, 14 Drawing Figures

Fig.3
(A)
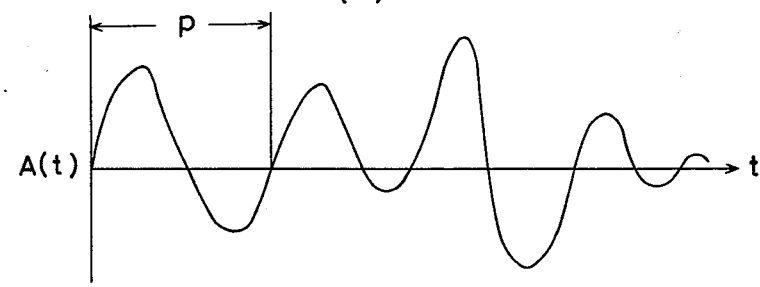
(B)
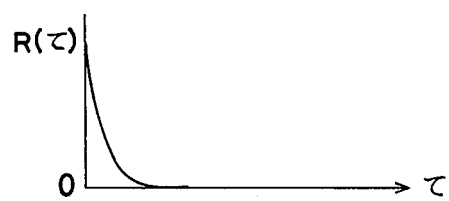
(C)
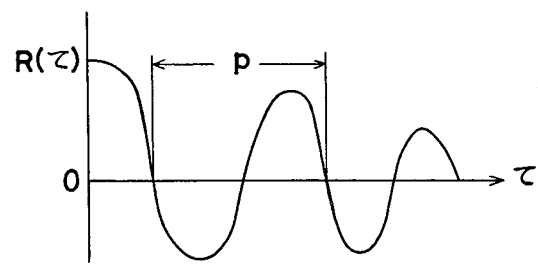

METHOD AND APPARATUS FOR INSPECTING AN INTERNAL PRESSURE OF HERMETICALLY SEALED CONTAINER

This invention relates to a method and apparatus for inspecting the internal pressure of hermetically sealed containers, particularly to a method and apparatus for inspecting non-destructively the internal pressure by compulsorily vibrating a can end forming a part a bottle or a canning container, for example, a hermetically sealed metallic container such as a can for canning, at least a part of which is made of an elastic material.

In the case of canning or bottling, the foods are generally canned or bottled at the specified vacuum condition as high as 40 to 60 cm Hg of the internal pressure for the purpose of preventing quality change and decomposition of foods, however, the degree of vacuum is lowered due to the leakage of contents through a pinhole on the can or end or due to generation of gas because of quality changes or decomposition of the contents. Moreover, in case of canned beer or canned carbonated beverage drinks, the contents are canned under an increased pressure but a leak will sometimes cause a drop of pressure conditions. Such insufficient pressure cans must be eliminated by detection at the time of manufacturing. As a method of detecting such faulty cans, there is a well known method, utilizing such a principle that the natural vibration induced when a part of the hermetically sealed container is vibrated compulsorily is determined by the function of the internal pressure. This method is already filed in Japan as the published or open patent application, Sho 49-7192 and, Sho the published or open patent application Sho 49-7192 and Sho 49-34376, the last mentioned application corresponding to U.S. Pat. No. 3,802,252.

In the former case, the can end of a hermetically sealed can is directly hit by a hitting stick consisting of a metal stick having a length of 20 cm and a metallic ball having a diameter of 1 cm provided at the end of the stick, thus exciting compulsory vibrations at the can end and thereby the degree of vacuum condition of the can is discriminated automatically from the attenuation period of natural vibration induced by this compulsory vibration. In the latter case, an impulse is applied to the can end, then the sound signals of the initial compulsory vibration generated from the can end of the hermetically sealed container and resulting natural damped oscillation are detected by a microphone through the conversion from sound waves to an electric signal, thereafter the measured frequency related to the natural damped oscillation after the attenuating period of the initial damped oscillation, namely after the gate period is extracted by a filter, thereby the internal pressure is discriminated in accordance with such frequency.

Moreover, the former method is lacking in reliability and has a disadvantage that requires a considerable period for discrimination because the manual hitting condition considerabley fluctuates in accordance with the can setting condition, there is a probability of mis-discrimination for the cans having a plurality of resonance frequencies since the resonant frequency of the can is searched by the sweep using a driving frequency, and moreover a sufficient period is necessary for sweeping entire range of frequencies which is also changeable. On the other hand, the latter method also has a disadvantage that cannot ensure quick and accurate discrimination because discrimination is performed on the basis of the natural damped oscillation after the gate period, two or more frequency components are, in the case of cans having a plurality of resonant frequencies, combined into the combined waveform with deformation of waveform as mentioned in the former method, and thereby natural vibration extraction accuracy by means of a filter is deteriorated regrading discrimination accuracy and moreover ambient noise, for example, noise generated from other machinery such as a belt-conveyor is detected by the microphone and such noise directly causes a measuring error when such noise forcibly includes the component of the vibration frequency range of the relevant can etc.

Here, it is well known that the sound detected and received by the microphone, if it is a simple sound, can be discriminated with excellent high accuracy; but for the ordinary apparatus, it cannot be said to be a simple sound. Usually such sound includes harmonics of the natural damped oscillation frequency of the can end and unwanted vibration sounds such as induced noise of excitation pulse etc. and therefore the detected waveforms are often distorted in a complicated manner. Distortion of detected waveform results in the probability of mis-discriminating a faulty product from a good one, as well as deteriorating discrimination accuracy for the internal pressure of the can.

For example, the can end containing a fruit juice which is the typical can having a diameter of 5 cm and volume of 250 cc has the resonant natural frequency of about 2 KHz in the case of good condition or about 1 KHz in case of non-vacuum and faulty condition.

If the detected sound the faulty can includes harmonic component, it just coincides with the frequency of a good can. Therefore, if the rate exceeds a specified value, a fault can is misdiscriminated as a good can. In addition, an impulse which excites the can end generates a noise on the microphone due to the electro-magnetic induction effect, thus mis-discrimination is caused by migration of such noise into the signal corresponding to the detected sound wave. Particularly, when inspecting the cans housed in a cardboard box from the outside, the sound is drastically attenuated by the cardboard box and therefore it is necessary to reduce the induction noise as much as possible.

The configuration of the most typical pressure sensing head 10 which is widely used now is shown in FIG. 1. In this Figure, a single pulse, which is similar to a half-cycle of a sine wave, having a pulse width of 0.5 mS, voltage of 200 V and current of several tens amperes is applied to a magnet coil 12 from a pulse generator not illustrated in FIG. 1. At this time, a can end 14a of a hermetically sealed can 14 is compulsorily excited by the magnetic flux pulse generated at the magnet coil 12 and the can end 14a, when it is made of an iron-based tinplate or tin-free steel, receives momentarily an attractive force, or a repulsive force is generated between an eddy current induced on the can end 14a due to mutual electro-magnetic induction effect and the magnet coil 12, when it is made of non-ferromagnetic material such as aluminum, thereby the can end 14a is excited by receiving an impulsive force as if hit by the abovementioned hitting stick, thus the can end 14a results in free vibration at the resonant natural frequency corresponding to the elastic stress due to a pressure difference between inside and outside, generating a vibration sound.

This vibration sound reaches the microphone 18 through the sound guide tube 16 provided at the center of a bobbin 16a of the magnet coil 12 and then converted into an electrical signal. The reason why the microphone 18 is provided at the area about several centimeters or more apart from the magnet coil 12 via the sound guide tube 16 is that an induced noise must be made less as mush as possible as explained above, however, this attempt brings about the following disadvantages.

Namely, the sound guide tube 16 forms a cavity pillar having an open end and closed end at the lower and upper sides, respectively and therefore has a function as the resonator. For this reason, this sound guide tube strongly responds in some cases to a certain frequency and its harmonics or in some reversed cases it shows extremely deteriorated sensitivity for a particular frequency. Thereby, the distorted waveform shown in FIG. 2(B) or its harmonics shown in FIG. 2(C) are detected, making impossible the normal discrimination.

It is an object of this invention to provide an innovative method and apparatus for inspecting the internal pressure of a hermetically sealed container which results in little error for unwanted harmonics migrating into the compulsorily excited vibration sound of the elastic wall of the container, plurality of resonant frequencies, induced noise and external noise.

It is another object of this invention to provide a method and apparatus for quickly inspecting the internal pressure of a hermetically sealed container with high sensitivity and accuracy.

It is other object of this invention to offer a method and apparatus for inspecting the internal pressure of a hermetically sealed container, which discriminates the adequacy of the internal pressure in accordance with the measured period guided from self-correlation function obtained through analysis and operation process for the free vibration excited at the elastic wall of a hermetically sealed container.

It is a further object of this invention to provide a method and apparatus for inspecting the internal pressure of a hermetically sealed container, which performs a discrimination process by the measured period in the form of arithmetic operation process by the comparison in the digital counting.

It is a still further object of this invention to provide a method and apparatus for inspecting the internal pressure of a hermetically sealed container, which outputs a level of detected signals after comparison and operation with the previously set lower limit level, simultaneously with analysis and operation of detected signals related to free damped oscillation excited at the elastic wall of a hermetically sealed container.

It is an additional object of this invention to provide a pressure sensing head in such a sensing head comprising a hitting device and vibration detecting device in a unit, wherein the vibration detecting device is always kept under the best conditions by providing the best environmental condition for the vibration detecting device so that it does not receive the bad influence of the hitting device as often as possible and by establishing on adequate setting position for the hitting device.

Further additional objects of this invention will become apparent from the detail explanation given in connection with the accompanying drawings.

FIG. 3 (A) shows an example of waveform for explaining the self-correlation which this invention employs.

FIGS. 3 (B), (C) respectively show an example of the characteristic curve related to the self-correlation function of the random waveform and periodic waveform.

Figure 4:
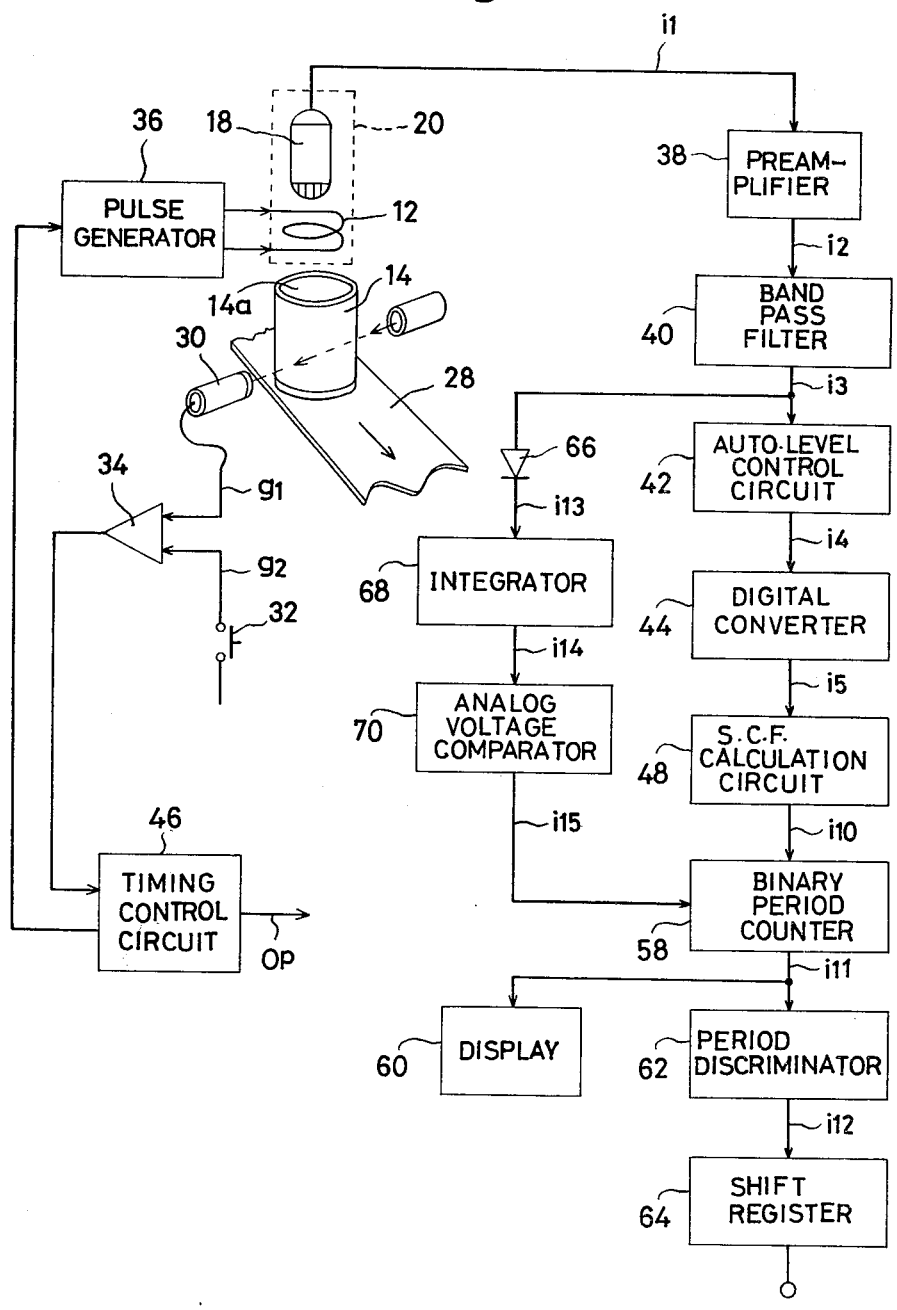

FIG. 4 is a block diagram of this invention in the form of flow chart.

FIG. 5 is a vertical cross section at the center of the pressure sensing head.

Figure 6:
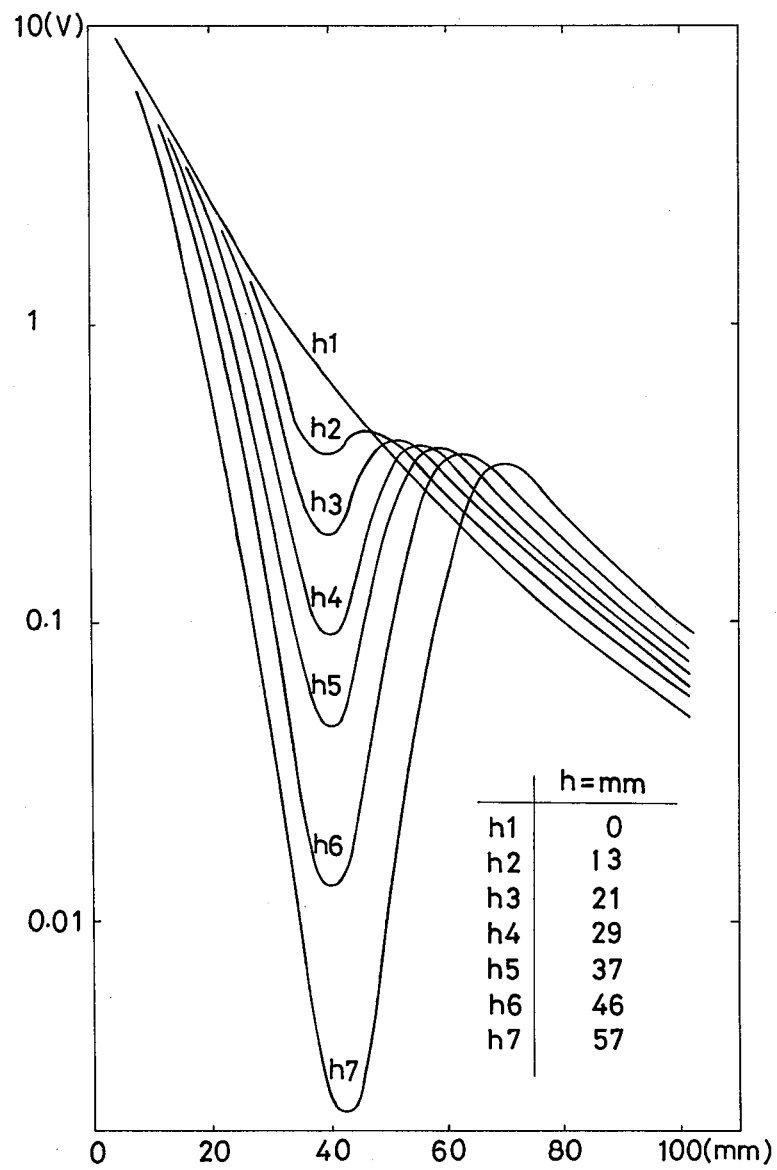

FIG. 6 shows graphs of experimental data indicating the extent of alleviation of induced noise by the cylindrical shield in accordance with the change of dimension of the length thereof.

Figure 7:
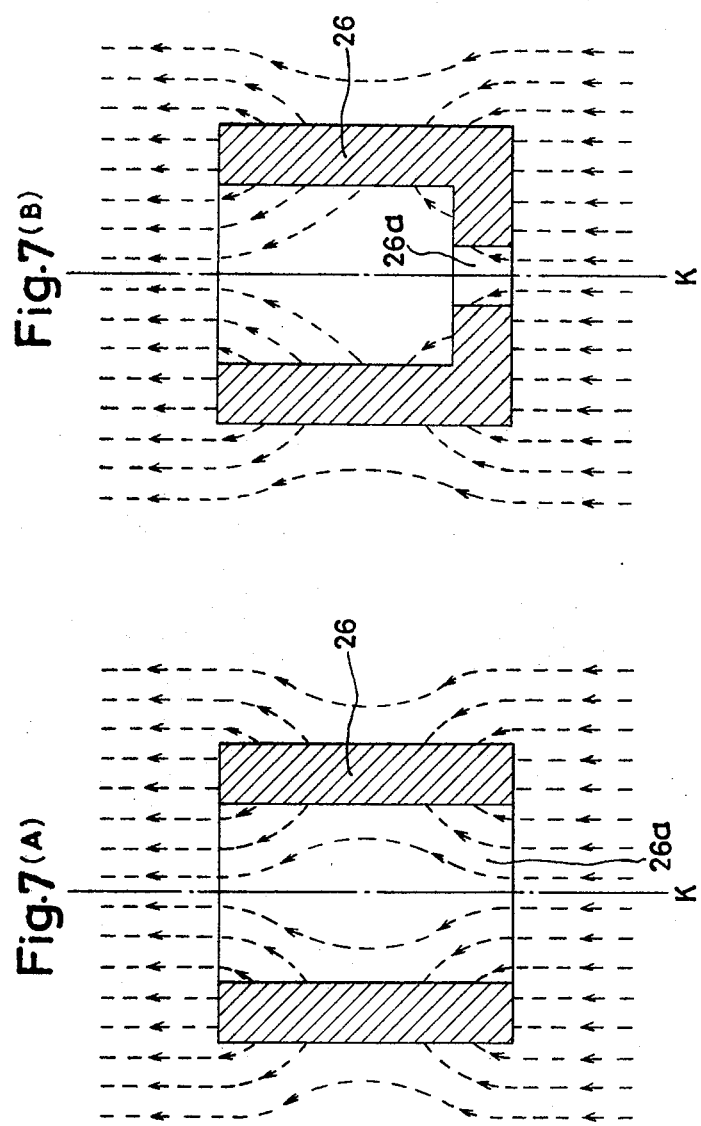

FIG. 7 (A), (B) show the estimated distribution of lines of magnetic force around the cylindrical shield. FIG. 7 (A) is adopted to the cylindrical shield having the upper and lower ends in the same diameter, while FIG. 7 (B) is adopted to the cylindrical shield having the lower end which is reduced in diameter in the form of a closed chain rather than the upper end.

Figure 8:
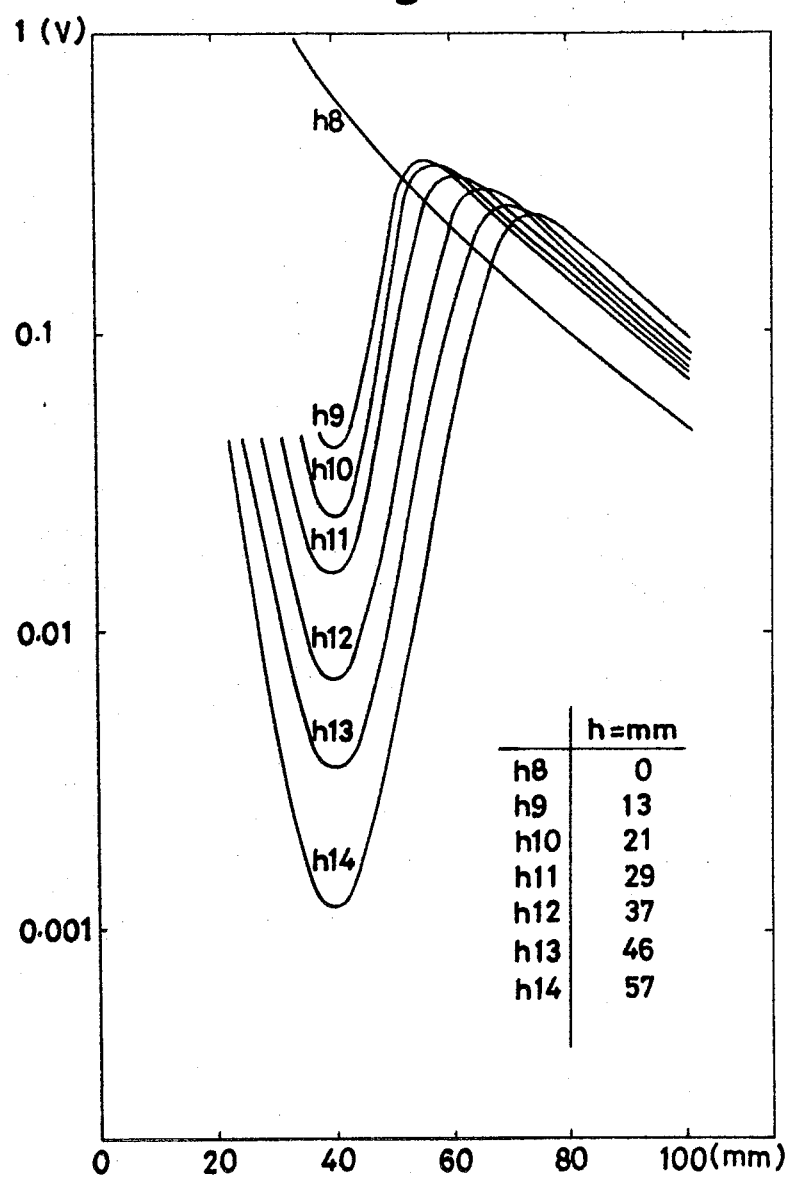

FIG. 8 shows graphs of experimental data indicating the extent of alleviation of induced noise of the cylindrical shield shown in FIG. 7(B) under the same conditions as in FIG. 6 in the dimension of height (or length).

Figure 9:
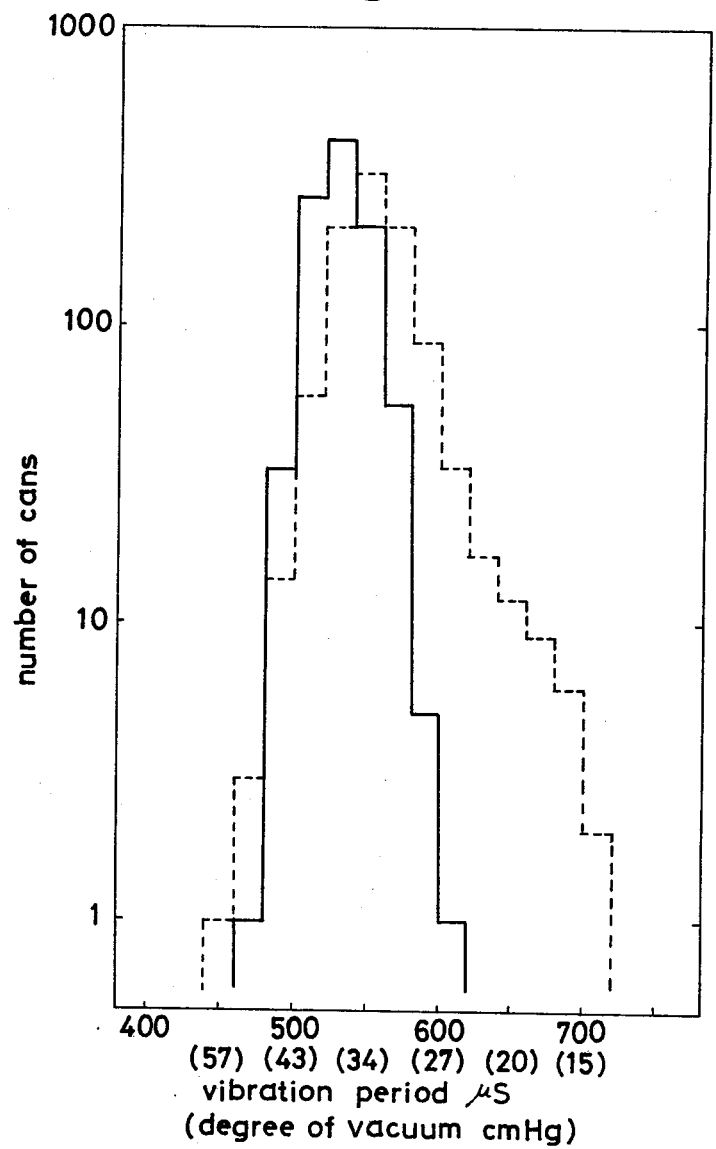

FIG. 9 shows graphs of comparing distribution of can end vibration periods detected and measured respectively by the pressure sensing head related to this invention and the known prior art.

Figure 10:
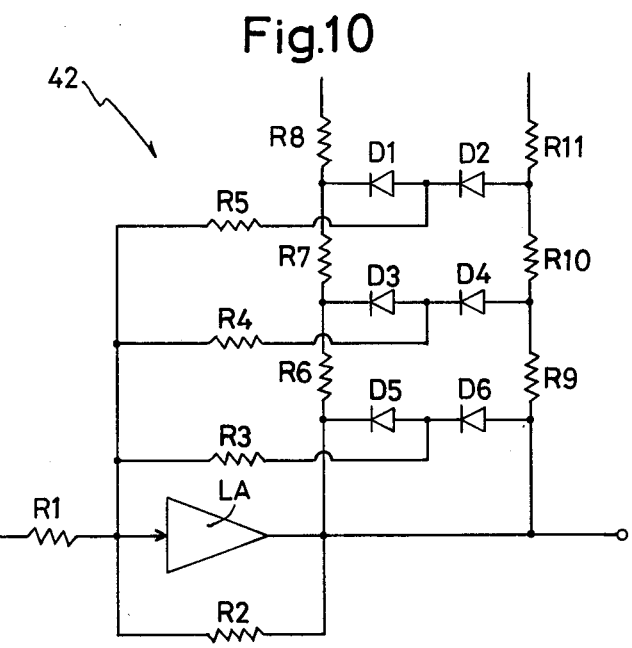

FIG. 10 is an example of the automatic level control circuit forming a part of this invention.

Figure 11:
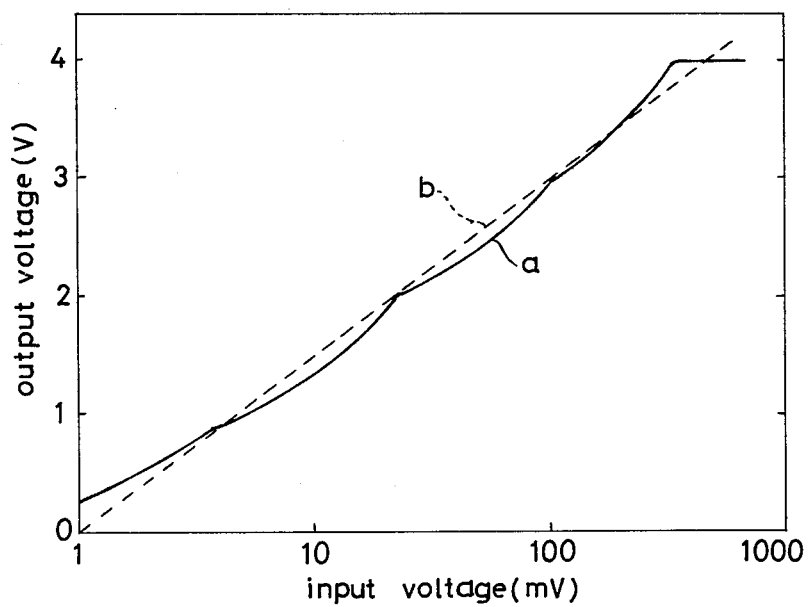

FIG. 11 is a logarithmic graph indicating a characteristic curve and ideal logarightmic characteristic straight line of the automatic level control circuit.

Figure 12:
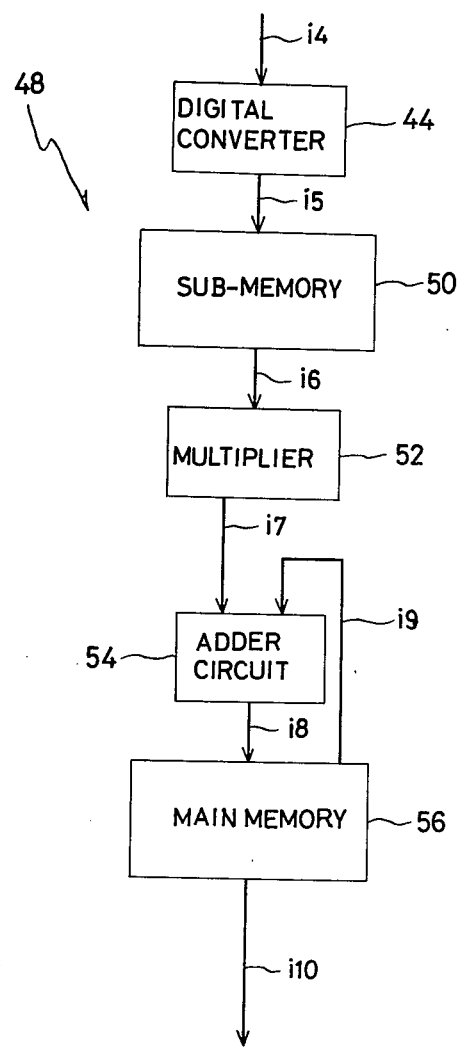

FIG. 12 is a block diagram of the digital self-correlation function circuit.

Figure 13:
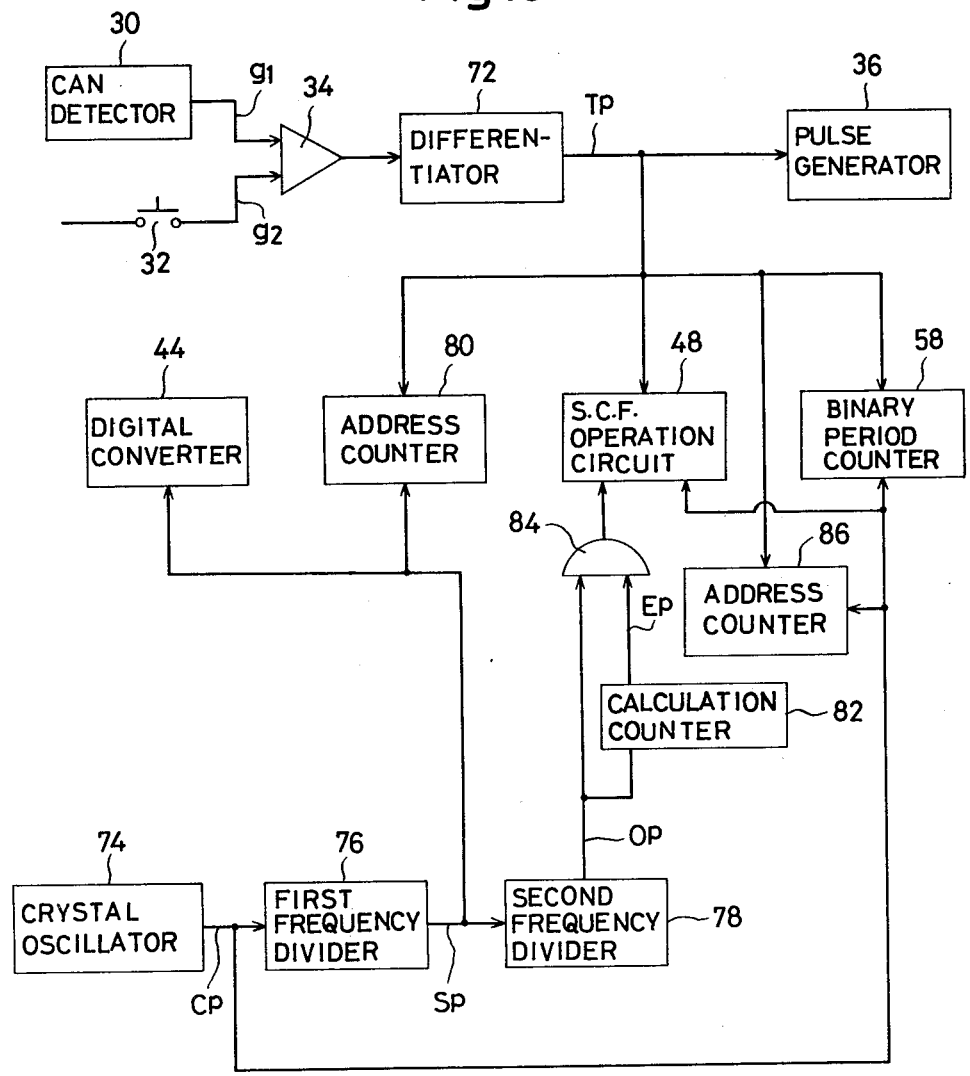

FIG. 13 is a block diagram of the timing control circuit.

Figure 14A:
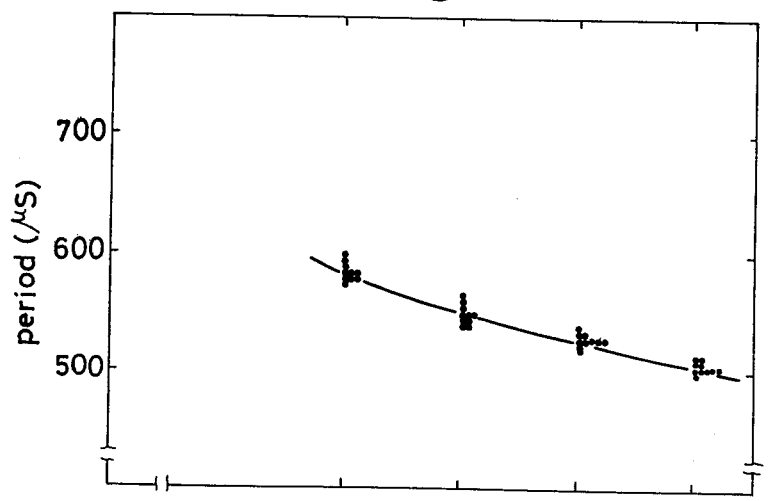

FIGS. 14(A) (B) respectively show period measurement graphs when the apparatus of this invention is used or when the existing general purpose universal counter is used.

When briefly summarizing this invention, the present invention has the following feature that a sound wave of free damped oscillation excited at the elastic wall of a hermetically sealed container is converted and detected as an electrical signal, analysis is performed for a natural self-correlation function of this detected signal by using logical operation circuits, thus, adequacy of an internal pressure is discriminated the measuring period of such function.

In this invention, in order to pick up as mush as possible only the pure sound wave related to free damped oscillation excited and generated at the elastic wall of a hermetically sealed container and to convert the sound wave into an electrical signal, a sound absorbing material is used at the sound reflecting surface thus attenuating the reflected sound in view of preventing resonance generated by the interference due to the reflected wave at the pressure sensing head and the succeeding incoming sound, simultaneously it is attempted to provide a magnetic shield using ferromagnetic material in order to eliminate induced noise which is another problem.

However, such attempt is accompanied by various technical difficulties which result from the necessity of an open end which is essential for taking the detected sound to the microphone which is a vibration detecting device being protected within the magnetic shield.

A free vibration succeeding the initial compulsory vibration due to physically impulsive excitation of an elastic wall of a hermetically sealed container, for example a can end (hereinafter explanation will be given for this can end) is a natural damped oscillation of the can end having a particular period and showing a vibration in the same phase even after a lapse of time which is an integer time of a period. On the other hand, an external noise generally has transient nature and therefore is less periodic, and it is rare that the phase of vibration is the same even after a lapse of time of several periods. The present invention is fundamentally based on the qualitative principle guided from similarity between waveforms appearing for each period of the free vibration component, for which only the free vibration component is extracted by the arithmetical operation process from the vibration waveforms (waveforms distorted by noise etc.) of the can end detected focusing on different characteristics of these vibrations mentioned above.

For the qualitative measurement of similarity of the abovementioned waveforms, the self-correlation method is used, and hereinafter this self-correlation method will be explained.

For example, the self-correlation function $R(\tau)$ of the waveform $A(t)$ shown in FIG. 3 (A) is defined as follow.

$$R(\tau) = \lim_{T \to \infty} 1/T \int_0^T A(t)A(t - \tau) \, d\tau \quad (1)$$

Where, $\tau$ is time shift, while T is observation time.
In addition, t is a continuous time.

This self-correlation function $R(\tau)$ shows quantitative similarity, as the normal probable process, between the waveform which changes with some probability and a waveform which is the same as such waveform but shifted in timing, and if the waveform $A(t)$ has a periodic nature, it coincides with the waveform which is shifted in timing from the original waveform because of their similarity each time when the period P of the waveform $A(t)$ coincides with the shifted time $\tau$ or when $\tau$ becomes an integer time of P, and resultingly the value of $R(\tau)$ becomes that of the waveform shown in FIG. 3 (C) having the period which is the same as that of the original waveform. In the case of a random waveform having no periodic nature at all, when $\tau$ becomes larger than $0, R(\tau)$ rapidly closes to zero as shown in FIG. 3 (B) and there is no chance of indicating a periodic value.

Therefore, when the self-correlation function of the vibration of hitting sound of the can end is obtained for a considerably long period, non-periodic noise or quickly attenuating compulsory vibration at the time of hitting, harmonic vibration and vibration having plurality of resonance frequencies are considered as the random component, and only the natural vibration of the free vibration can be extracted as the periodic vibration.

The approximate equation of such equation (1) can be expressed as the equation (2) and it is a very useful equation which can be adopted to a digital computer.

$$R(k\Delta\tau) = 1/N \left\{ \sum_{n=1}^{N} A(n\Delta t) \cdot A(n\Delta t + k\Delta\tau) \right\} \quad (2)$$

Where $\Delta t$ is a computation interval in the relation with said equation (1).
$t = n \Delta t$, $\Delta \tau$ is the minimum unit of time shift,
$\tau = k \Delta t$, $k = 1, 2, 3, \ldots$, $n = 1, 2, 3, \ldots$
N is average number of times, $T = N \Delta t$, respectively.

Thus, the analysis and arithmetic operation processing method for the waveforms which is the basic principle of this invention has been explained above, and this invention will be explained below in the detail on the basis of the preferred embodiment of this invention.

This invention establishes synthetic system circuits as shown in FIG. 4 and FIG. 12 to FIG. 13, consisting of the circuit elements which will be explained hereunder sequentially.

Figure 1:
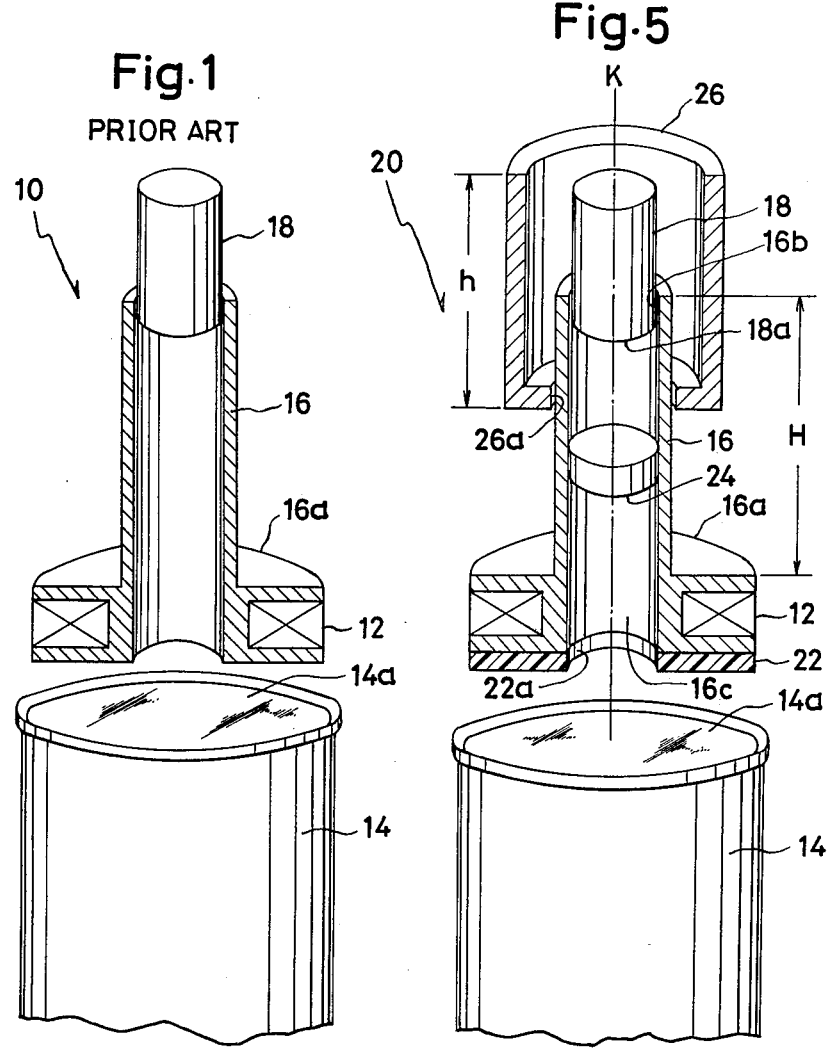
FIG. 1 is the vertical cross section at the center of a known pressure sensing head.

Namely, FIG. 4 shows a block diagram, in the form of flow chart, of an embodiment of this invention applied to cans for canned foods. The sensing head 20 is so configured as shown in FIG. 5 that sound absorbing materials 22 and 24 are attached in such a form as to block the interim between the lower surface facing the can end 14a of a coil bobbin 16a and a sound guide tube 16, in the known type of pressure sensing head 10 as shown in FIG. 1, having the configuration that the magnet coil 12 which operates as the hitting device is wound around the bobbin 16a mounted on the circumference of the lower end of the sound guide tube 16 in the form of flange a and simultaneously a sound receiving part 18a of a microphone 18 which operates as a vibration detecting device is inserted at the upper open end 16b of the sound guide tube 16. A cylindrical magnetic shield 26 is mounted in a manner surrounding the microphone 18. The sound absorbing materials 22 and 24 are made of porous and permeable materials which are generally used as the sound absorbing materials, such as permeable formed polyulethane, felt, cloth, cotton, glass fiber or soft tissue, and by adequately selecting the amount of this material, sufficient effect for preventing resonance can be obtained. In the case of this embodiment, the sound absorbing material 22 has a diameter of 5 cm as in the case of the coil bobbin 16a and the part at the lower open end 16c which is the entrance of the sound guide tube 16 is provided with a hole 22a having the same diameter of 1.5 cm as the open end.

When the formed polyulethane is used as the sound absorbing material 22, the effect is admitted for the thickness of 3 mm or thicker, and when felt is used, for the thickness of 1 mm or thicker. Practically, doubled thickness is sufficient. As far as the sound absorbing material 24 provided at the inside of the sound guide tube 16, when it is provided at the center of the sound guide tube 16 as shown in the Figure or when provided at the other position, for example, the position just before the sound receiving part 18a of the microphone 18 or the position blocking the lower end 16c of the sound guide tube 16, the sound absorbing effect was the same. Moreover, as the more effective method of providing the sound absorbing material, when felt is attached along the internal wall of the sound guide tube 16 in the thickness of 1 to 2 mm, the sound was less attenuated than the abovementioned method of blocking the inside of the sound guide tube 16 and the level of detected signal due to the same exciting impulse was 1.4 to 2 times.

The induced noise can generally be eliminated by surrounding the entire part of the electronic circuit with a container made of iron or ferromagnetic material which is an alloy of iron or by providing a partition type shield plate against the incoming direction of the lines of magnetic force.

However, in the case of the pressure sensing head 20 for the present hitting inspection, it is necessary to provide an opening on the magnetic shield for the sound receiving part 18a of the microphone 18 and since the sound incoming direction is the same as that of the lines of magnetic force, it is difficult to simply employ the existing shielding method.

As the first step, an experiment was conducted in order to know the shielding effect of a cylindrical shield 26 having its lower open end 26a disposed toward the incoming direction of the lines of magnetic force.

In FIG. 5, the center position of the height h of the cylindrical shield 26 is fixed at the position elevated by the distance H from the upper surface of the coil bobbin 16a, the microphone 18 being moved along the center axis K of the magnet coil 12 and cylindrical shield 26, thereby the level of noise induced at the microphone 18 has been measured. The result is shown in FIG. 6. In this Figure, the horizontal axis (X-axis) represents, in units of mm, the distance of the diaphragm (not illustrated) attached to the sound receiving part 18a of the microphone 18 from the upper surface of the coil bobbin 16a, while the vertical axis (Y-axis) represents, in units of volts, the level of induced noise. The curves h1 to h7 are the characteristics when the height h of the cylindrical shield 26 is changed. The value is shown in the same Figure.

As shown in this Figure, the noise level becomes minimal at almost the center in the height direction of the cylindrical shield 26.

The longer the height of the cylindrical shield, the larger the shielding effect. It has also been known that noise level can be reduced to 1/100 or less by adequately selecting the height h.

The cylindrical shield used for the experiment is a steel pipe for electrical wiring having an inner diameter of 25 mm and a thickness of 1 mm, and difference was as small as can be considered as the measuring error even when a steel pipe for gas distribution having the doubled thickness was used.

If actually ignorable noise level is considered as 1/10 of detected signal level of the vibration sound of can end 14a, since the sound signal is about 50 mmV, the height h of the cylindrical shield 26 must be that corresponding to the interim value of the curves h6 and h7 in FIG. 6, namely, about 50 mm or more.

From the result of the above experiment, it can be estimated that the distribution of lines of magnetic force around the shield can be shown by the dotted lines in FIG. 7 (A) when the cylindrical shield 26 is placed in the field intensity which is parallel with the axis K of the shield. In other words, the lines of magnetic force entering into the lower open end 26a which is the opening of the cylindrical shield 26 is a little absorbed by the material of the cylindrical shield 26 after it enters the inside of it. When the lines of magnetic force goes out of the cylindrical shield 26 from the upper end of it, the lines of magnetic force are also a little going out of it not only from the end of the cylindrical shield 26 but from the inside of the cylindrical shield 26. However, when the cylindrical shield 26 is short, the line of magnetic force is not absorbed by the material of the cylindrical shield 26 and the magnetic flux passing inside of the cylindrical shield 26 seems to be increased.

When the diameter of the lower open end 26a of the cylindrical shield 26 in the incoming direction of the lines of magnetic force is made as small as possible as shown in FIG. 7(B), and when the number of lines of magnetic force entering into the cylindrical shield 26 is reduced, distribution of the lines of magnetic force in the cylindrical shield 26 might become the minimum as shown by the dotted lines in the same Figure.

In order to make small the diameter of the lower open end 26a of the cylindrical shield 26 used for the experiment shown in FIG. 6 in the incoming direction for the lines of magnetic force, a ring-shape plate made of iron was provided and then the experiment which was the same as that shown in FIG. 6 has been conducted. The ring-shape plate has a thickness of 1 mm which is the same as that of the cylindrical shield 26 and the opening has a diameter of 10 mm. This diameter has been made as small as possible within the range of not deteriorating the sound detection sensitivity. The result is shown in FIG. 8. The curves h8 to h14 in the same Figure show the characteristic when the height of the cylindrical shield 26 is changed and these correspond to the curves h1 to h7 in FIG. 4.

Figure 2:
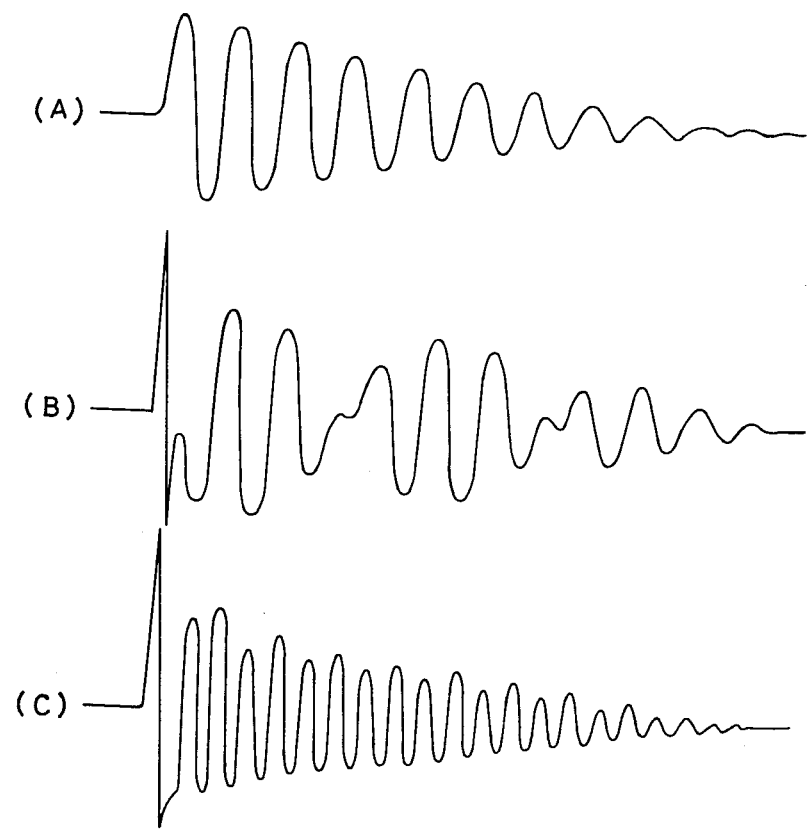
FIG. 2 shows inspected elastic vibration waveforms of the can end. In this Figure, (A) is the natural damped oscillation waveform of a simple sound not including a resonant component and induced noise; (B) is a distorted waveform of such simple sound including a beat component due to resonance and induced and; (C) is a waveform of harmonic vibration due to resonance and induced noise.

By comparing the results of both experiments explained above, it can be known that the induced noise can be reduced moreover to the extent expressed by the fraction number by making small the area of lower open end 26a, and the can end vibrating waveform when the necessary height of the cylindrical shield for ignoring induced noise is selected to be 40 mm which is the interim value of curves h12 and h13 shown in FIG. 8 has been detected as the damped oscillation of a simple sound in FIG. 2(A).

Regarding the pressure sensing head 20, an example of having improved actually the can inspection and discrimination accuracy will be shown below.

The automatic hitting inspection machine which is an internal pressure inspection machine is set in the final process of the canning food production line in which a fruit juice of 250 cc is canned, and then hitting inspection has been conducted for normal products of 1000 cans by using the pressure sensing head 20 related to this invention and the known pressure sensing head 10. Thus, distribution of the vibration period of the can end 14a measured has been searched and compared for each can. The result is shown in FIG. 9. In this Figure, the horizontal axis represents the vibration period and corresponding degree of vacuum in the can, while the vertical axis represents the number of cans satisfying the abovementioned vibration period range using the logarithmic scale. The solid line represents the measured value using the pressure sensing head 20 related to this invention, while the dotted line represents values obtained by using the known pressure sensing head 10.

As is apparent from this Figure, distribution of the vibration period is reduced to about ½ by using the pressure sensing head 20. When the degree of vacuum in the cans having completed the measurement with both pressure sensing heads was measured with the vacuum meter of the Bourdon's tube type, all cans showed the degree of vacuum within the range from 32 to 43 cm Hg. Therefore, it is estimated that the measurement and discrimination accuracy is ±7 cm Hg when the pressure sensing head 20 is used, while ±15 cm Hg when the existing pressure sensing head 10 is used.

As far as the harmonic vibration preventing effect is concerned, in order to perform the inspection with non-vacuum cans which are more likely to cause harmonic vibration, a total of 100 cans bored arbitrarily at the body with a driling machine were prepared. Thus, measurement was carried out using both the pressure sensing head 20 related to this invention and known head 10. The result is shown in the following table.

| Range of vibration period | | Pressure sensing head (20) | Pressure sensing head (10) |
|---|---|---|---|
| 400 | 499 μs | 0 (can) | 2 (can) |
| 500 | 599 | 0 | 8 |
| 600 | 699 | 0 | 1 |
| 700 | 799 | 0 | 0 |
| 800 | 899 | 0 | 0 |
| 900 | 999 | 18 | 18 |
| 1000 | 1099 | 52 | 45 |
| 1100 | 1199 | 27 | 24 |
| 1200 | 1299 | 3 | 3 |

According to the above table, about 10% of the non-vacuum cans are mis-discriminated as the good cans due to harmonic vibration when the existing pressure sensing head 10 is used but mis-discrimination does not occur when the pressure sensing head 20 is used.

Since the pressure sensing head 20 is so configurated as described above, elastic vibration of the can end 14a can be detected as the natural damped oscillation of simple sound by eliminating resonance between the sensing head 20 and can end 14a or in the sound guide tube 16, and by alleviating induced noise level, thereby discrimination accuracy of the automatic hitting inspection device and there is no chance of mis-discriminating the non-vacuum cans as the good one.

Numeral 14 in FIG. 4 is a can to be inspected and is carried by a conveyor 28. Among the circuit element group shown in this Figure, 30 is a pair of can detectors which sandwich the conveyor 28 and provide a photo-electric detector consisting of a light source comprising a small lamp and light receiver comprising photo-transistor. Numeral 32 is a manual push button switch for manually performing the operation acknowledgement test of the whole system. The operation output signal g2 sent from this manual push button switch 32 is input to the OR circuit 34 together with the detection output signal g1 from the can detector. Numeral 36 is a pulse generator consisting of a capacitor and thyristor circuit which operates when the can detector 30 detects that the can 14 comes to the position just below the pressure sensing head 20 or when the manual push button switch 32 is pushed and sends the power pulse to the magnet coil 12, thus compulsorily vibrating the can end 14a. Pulse width can be changed by combining adequately the electro static capacitance and coil inductance and it is determined to the most adequate one in accordance with the can material etc.

The microphone 18, which operates as a vibration detector, detects the sound wave which is generated when the can end 14a vibrates and outputs such sound wave in the form of the electrically detected signal i1. Numeral 38 is a preamplifier which linearly amplifies the detected signal i1 and 40 is a band pass filter composed of the general purpose operational amplifier using resistors, capacitors and ICs. This filter 40 attenuates and shuts off frequencies other than the natural vibration frequency range of the can end 14a included in the detected signal i2 and moreover reduces induced power supply noise migrated into the detected signal i1, impulsive high frequency noise and ambient noise. Although the noise including the frequency component within the pass band of this filter 40 passes this filter 40, it is erased by the analysis and operational processing which the present invention employs.

Numeral 42 is an automatic level control circuit which compensates the variation of detected signal due to the difference in distance between the pressure sensing head 20 and can end 14a and level difference of the generated sound due to the difference in the amount of can content. This circuit is also provided with an amplitude limiter of the logarithmic compression type which does not result in delayed response. In this means, the output detection signal i4 waveform is compressed at the head as compared with the input detection signal i3. However, in the case of this invention, amplitude linearity is not required and only required is variation in period of zero cross of the signal waveform. This amplitude limiter includes a linear amplifier using ICs and uses the polygonal line approximation function generator utilizing the diode clipper shown in FIG. 10 where many resistors R and diodes D are wired in combination. According this generator, approximate logarithmic compression can be made for an input voltage, for example, 1 mV to 500 mV as shown by the polygonal curve line a in FIG. 11. In FIG. 11, the straight line b indicates the reference line of the ideal logarithmic characteristics. This logarithmic compression treatment for this detected signal i3 facilitates calculation of the next self-correlation function by making less level fluctuations and alleviates the error more than in the case of executing calculations of self-correlation function with the detected signal i3 used without transformation, since the distorted portion of the waveform due to plural resonance frequency vibrations and the harmonic wave component due to compulsory vibration just after the excitation is compressed strongly.

Numeral 44 is a parallel comparison type 4-bit analog to digital converter consisting of a voltage comparator and binary coding logic. This circuit converts the detected signal i4 which is an analog voltage signal into a digital detected signal i5 for each minimum unit $\Delta\tau$ of the time shift explained in the calculation formula for obtaining such self-correlation function, namely each time the sampling pulse of 5 μs, for example, from the timing control circuit 46 which will be described later.

Numeral 48 is a self-correlation function calculation circuit and it is shown in detail in the form of the block diagram of FIG. 12. In the circuit configuration element group shown in FIG. 12, 50, for example, is a sub-memory consisting of the random access memory of a large scale integrated circuit having the capacity of 4 bits×256 words, and this sub-memory is capable of storing the detected signal i5 which is converted into the 4-bit pure binary code by sampling at the analog to digital converter 44. At the time of storing, the content of memory is sequentially renewed and transferred from the oldest digital data signal i6 and the latest 256 digital data signals i6 are always stored sequentially in the memory. Numerals 52 and 54 are a multiplier and adder respectively, each of which is a digital operation circuit consisting of AND and OR gates using an TTL integrated circuit, logic circuit elements and register. Numeral 56 is a main memory having the capacity of 13 bits×256 words.

When an order pulse OP is issued as the calculation start signal from the timing control circuit 46 described later which is started by the can detector 30 and push button switch 32, the content, stored in the sub-memory 50, namely 256 data signals i6 are read out at a high speed sequentially from the digital data signal related to the oldest detection signal i5 in the timing. Thus, multiplications with the first digital data signal i6 are respectively performed at the multiplication circuit 52. As a result, the multiplied digital signal i7 becomes the added digital signal i8 through the adder circuit 54 and then stored in the corresponding address of the main memory 56. By this processing, calculation of N=1 in the parentheses { } of the aforesaid equation (2) is performed. After the calculation of N=1, keeping the calculation interval of $\Delta t$, 0.15 ms, for example, from the order pulse OP as the first calculation start signal, succeedingly the order pulse OP as the next calculation start signal is issued from the timing control circuit 46. Thereby, the calculation of N=2 is started. As in the case above, multiplication with 256 data corresponding to the digital data signal i6 before such timing is carried out. Then, addition with the feed back data signal i9 which is obtained by each time by drawing the precedingly stored contend in the main memory 56 is performed at the adder circuit 54 and the result is respectively stored in the initial address of the main memory 56. Succeedingly, operation is carried out as in the case above at an interval $\Delta t$, for example, 0.15 mS. When the value of N increases and reaches to the precedingly specified value of N, for example, in this embodiment, N=64, above operation completes. At this time, the contents in the main memory 56 becomes such a value within the parentheses of the equation (2), for example, the value in the case of N=64.

Here, said memory content is divided by N as shown in the self-correlation function equation (2). However, in the case of this invention, only the period of function is taken into consideration without relation to the function value itself. Therefore, the operation of dividing it with N can be omitted.

The main memory 56 also extracts only the sign bit as an output and considers it as the gate signal i10. Thereby, the existing procedures of converting the memory content into an analog signal with a digital to analog converter and moreover obtaining the gate signal with the zero cross switch can all be omitted, thus making rare error generation.

In the circuit elements shown in FIG. 4, 58 is a binary period counter consisting of TTL ICs. 60 is a display, for example, consisting of 7-segment indicator. When the self-correlation function operation unit 48 completes operations, the content of sign bit of the main memory is read out, for example, from address 0 to 1, 2, 3, ... 255 sequentially. Then, the gate of counter 58 is opened by the gate open instruction signal i10 which is issued when the read out content reaches for the first time the zero cross level where the value changes to negative from positive, and counting of the clock pulse CP which is the same as the read-out clock pulse CP of the main memory 56 is started.

Succeedingly, when the value reaches the zero cross level where it returns to positive from negative and then changes to negative from positive, the gate close instruction signal i10 closes the gate of counter 58, thereby operation completes. Operation for one cycle thus completes. When the counted value of counter 58 is considered as Cn, operation of $Cn \times \Delta \tau$ brings about the average vibration period of the initial signal for the $N \Delta t$ time, namely the free vibration of the can end 14a. The minimum unit $\Delta \tau$ of the shifted time is fixed to a constant value, a value of Cn is directly displayed on the display 60 as the period count signal i11 of the self-correlation function. If a vibration period is long and therefore the gate of counter 58 is still not closed even when reading completes up to the final address of the main memory, for example, up to address 255, display of the counter 58 proceeds up to a certain value larger than 256, for example, up to 300 and then stopped, thus indicating that the present vibration has such a long period as making impossible the measurement.

Numeral 62 is a period discriminator, namely, a digital comparator which allows free setting of the fault discrimination limit value Co of the cans 14 by operating the manual digital switch provided on the operation panel. This circuit compares the set value Co and counted value Cn and outputs a discrimination signal i12 indicating no good when $Co \leqq Cn$. 64 is a shift register for delaying the discrimination signal i12. When Cn becomes equal to Co (Cn=Co) while it is increasing, the discrimination signal i12 is issued. This discrimination signal i12 is delayed by the shift register 64 for the period as long as the can is moved to the position of the mechanical can rejecting system (not illustrated) in synchronization with the movement of conveyor 28 carrying the can 20, thus driving the not illustrated can rejecting system. As this can rejecting system, a mechanical can pushing-away device is used, where the cans are blown away by an air jet, or removed by a magnet or air cylinder.

In FIG. 4, a diode 66, integrator 68 and analog voltage comparator 70 which are sequentially employed to the detection signal level discrimination circuit connected in parallel in order to branch the detection signal i3 and finally provide an output to the counter 58 are circuit elements for detecting no signal condition in such a case where even when the can detector 30 detects a can 14, vibration of can end 14a cannot be detected by some abnormal condition, for example, the can 14 has fallen, or sound vibration is small since the can is deformed, or pulse generator 36, pressure sensing head 20 and its cable, preamplifier 38 or filter 40 is at fault. The detected signal i3 from the band pass filter 40 is branched and then rectified by the diode 66, thus extracted as a DC voltage signal i13. Then, simultaneously, an integrated voltage signal i14 which has been obtained by integrating the DC voltage signal i13 using the integral circuit 68 for such period as the calculation process for the self-correlation function conducted at the self-correlation function operation circuit 48 is compared with a DC voltage separately set by the analog voltage comparator 70. The gate of counter 58 opens with the gate open instruction signal i15 which is issued when the integral voltage signal i14 is lower than the set level, counting is carried out up to a specified value, for example, up to 400, and then it is displayed on the display 60 that measurement of period is impossible since no signal is detected or the detected signal level i3 is weak. Detection of such no signal condition is better to be conducted at the stage as succeeding as possible of the system in order to detect such condition of many processing stages but the stage after the automatic level control circuit 42 is not recommended for such detection since the signal level difference is reduced.

As mentioned above, every processing is subject to synthetic system control by means of the timing control circuit 46. This circuit will be explained in detail on the basis of FIG. 13. Among the circuit elements shown in this Figure, those given the same number as that in the other drawing respectively correspond to relevant circuit elements. 72 is a differentiator, 74 is a crystal oscillator which outputs a clock pulse CP of, for example, 0.5 μs. 76 is the first frequency divider which outputs the sampling pulse SP of 5 μS, for example, by dividing the pulse CP from the crystal oscillator 74. 78 is the second frequency divider which divides up to 0.15 mS, for example, the sampling pulse SP of 5 μS to be sent from the first frequency divider 76. The differential circuit 72 outputs a trigger pulse TP when the detection output signal g1 sent from the can detector 30 rises and when the operation output signal g2 which is output while the manual push button switch 32 is pushed rises in order to trigger the pulse generator 36 for exciting the can end and simultaneously resets the self-correlation function operation circuit 48, counter 58 and other circuit elements, thus placing them into the stand-by condition. Moreover, this circuit supplies the sampling pulse of 5 μS SP to the analog to digital converter 44 and address counter 80 for sub-memory 50, and then gives the pulse of 0.15 mS to the self-correlation function operation circuit 48 as the order pulse OP of the operation start signal. Simultaneously, the calculation counter 82 processes this pulse OP and the gate of gate circuit 84 closes with the end pulse EP of the close command which is issued when counting reaches 64, thereby supply of the pulse OP to the self-correlation function operation circuit 48 stops, thus completing operation.

Operational processing in the self-correlation function operation circuit 48 is performed by the clock pulse CP of 0.5 μS of the crystal oscilator 74, and moreover the address counter 86 of the main memory and counter 58 are also driven by the command of the clock pulse CP. These logic circuits are generally well known TTL type integral circuits.

The present embodiment of this invention has such a circuit configuration as allowing the following design application that, allowing, in order to moniter a deviation of the optical axis between the light source and light receiver of the can detector 30 or disconnected filament of the lamp, connection of an abnormal condition monitoring timer circuit to the detection signal g1 circuit, thereby such timer circuit operates when there is no light input to a light receiver for a considerably longer period than the cut-off time while the can having the maximum diameter as the object of measurement passes, for example, 1 second, causing the conveyor 28 to stop urgently and issues an alarm warning an abnormal condition, and allowing, in order to indirectly monitor an abnormal condition of the apparatus by this invention itself or the canning line to which this invention is adopted, connection of an abnormal condition monitoring counter circuit to the discrimination signal i12 circuit, thereby such counter circuit is composed of a 4-bit counter which counts fault discrimination signal i12 and is reset by good discrimination signal and a counted value comparison and discrimination circuit which can be set previously by a switch, and issues an abnormality detection signal only when such counter has counted continuously fault cans up to that which cannot be usually observed, for example, 8 to 16 cans continuously, urgently stopping the conveyor 28 and canning line with generation of alarm, wherein both abnormal condition monitoring timer circuit and abnormal condition monitoring counter circuit are connected at the NOR gate to the urgent command output relay driver and issues an urgent stop command signal to the conveyor 28 and not illustrated driving system of the canning system by closing the directly connected relay contact.

Moreover, it is also possible to freely comprise such design that an output signal is generated through operation of the break contact when current from the power supply is not conductive, by connecting an abnormal condition monitoring relay circuit, which monitors the non-operative condition of the apparatus related to this invention due to abnormal power supply and that caused when an operator has forgotten to turn on the power supply switch to the power supply for the logic circuits of the apparatus of this invention.

With such configuration, the present invention is capable of inspecting, on its design performance, up to 90 cans per second at high speed and is excellent in performance, reliability, fidelity and accuracy in great difference as compared with the known apparatus.

For the reference, a comparison was attempted under the following conditions by using both apparatus of this invention and a general purpose universal counter which is known as a typical period measuring instrument.

(Example of experiment)
Experimental condition:
1. As the inspection object, a total of four sample cans were prepared by selecting one sample can respectively from the cans containing fruit juice of 250 cc having a degree of vacuum of 30 cm Hg which is the discrimination criteria for good and faulty products, from those of 25 cm Hg as a faulty sample, from those of 35 cm Hg and 40 cm Hg as a good sample. These samples are respectively moved by the conveyor for the measurement of vibration period.
2. As the measurement system, a waveform which is not subject to the analysis and operational processing was used and moreover, in order to measure under the same condition as the apparatus of this invention, the output of automatic level control circuit 42 of this invention is branched to the outside and it is measured with a general purpose universal counter. At this time, however, in order to sufficiently attenuate compulsory vibration and plural resonant frequencies just after the excitation and measure only the natural vibration as much as possible, the waveform of initial 3 mS has been eliminated.
3. As the number of times of experiments, the same can was measured 10 times.

Figure 14B:
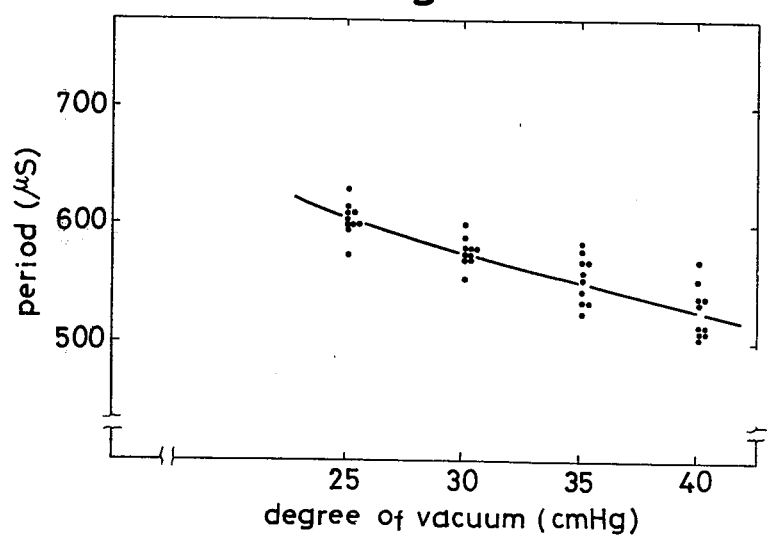

The result thus obtained by such measurement is shown in the graphs (A) (B) in FIG. 14.

The data of graph (A) is related to the apparatus of this invention, while (B) to the measurement by the general purpose universal counter.

In both graphs, the horizontal axis represents the degree of vacuum conditions in units of cm Hg, while the vertical axis, measured the vibration period of can end 14a.

On the occasion of comparing the accuracy of both measured values, the range of distribution of measured values at each degree of vacuum condition is shown in the following Table.

| Degree of vacuum Condition | B | A |
|---|---|---|
| cm Hg | General counter | Apparatus of this invention |
| 25 | 55 | 25 |
| 30 | 45 | 25 |
| 35 | 60 | 20 |
| 40 | 65 | 15 |
| Average | 56 | 21 |

As shown in the above Table, the distribution range of respective measured values of the can in each degree of vacuum condition is 1/2.5 or less than the values measured by the existing method. In addition, if discrimination criterion setting value is set at the mean value of measured values of cans under a degree of vacuum condition of 30 cm Hg, the existing method may mis-discriminate about 10% of the faulty cans under a degree of vacuum condition of 25 cm Hg as the good cans and resultingly about 20% of the good cans under a degree of vacuum condition of 35 cm Hg may be eliminated as the faulty cans. On the other hand, according to the method of this invention, there is little probability that the cans with deviation of a degree of vacuum condition of ±5 cm Hg is mis-discriminated.

When comparing the curves plotting mean values of both measured values of the graphs (A) (B) in FIG. 14, a difference about 30 $\mu$S can be observed between both curves. The reason can be estimated as the graph (A) is obtained by calculating the mean values about after 11 mS while the graph (B) is focusing on one period around 3 mS after excitation.

This invention can be applied effectively to such inspection as utilizing the natural vibration such as inspections for blowhole and cracks in cast iron, and for the degree of spreading a metal plate on a wall on which a metal plate is stretched and for the bonding condition at the rear side, and this invention can be adopted to every kind of non-destructive inspection method. Therefore, it is natural that this invention can cover the technical field other than a hermetically sealed container.

What is claimed is:

1. A method of inspecting the internal pressure of a hermetically sealed container consisting of the following steps: a free vibration is compulsorily excited on the elastic wall of a hermetically sealed container, the excited vibration is converted and detected as an electrical signal, the intrinsic self-correlation function of the detected signal itself is calculated through analysis and arithmetic operation including a processing for compressing logarithmicly the amplitude of the relevant detected signal, and the adequacy of the internal pressure is discriminated as an output in accordance with the measured period obtained from the relevant self-correlation function.

2. A method of inspecting the internal pressure of a hermetically sealed container as claimed in claim 1, wherein pre-processing facilities are provided for the detected signal before the analysis and arithmetic operation processings so that said detected signal is amplified by an amplifier and filtered by a band pass filter as the pre-processing.

3. A method of inspecting the internal pressure of a hermetically sealed container as claimed in claim 2, wherein said analysis and arithmetic operation processings include a processing for converting the detected signal into a digital signal.

4. A method of inspecting the internal pressure of a hermetically sealed container as claimed in claim 3, wherein said analysis and arithmetic operation processings include a processing for temporarily storing the digital signal related to the detected signal into a specified address in succession making possible a renewal.

5. A method of inspecting the internal pressure of a hermetically sealed container as claimed in claim 4, wherein said analysis and arithmetic operation processings include a processing for sequentially reading the temporarily stored digital data signal related to said detected signal and simultaneously multiplying regularly, following a specified equation being set previously.

6. A method of inspecting the internal pressure of a hermetically sealed container as claimed in claim 5, wherein said analysis and arithmetic operation processings include a processing for adding regularly the sequentially multiplied digital signals following the previously set equation for calculation.

7. A method of inspecting the internal pressure of a hermetically sealed container as claimed in claim 6, wherein said analysis and arithmetic operation processings include a processing for temporarily storing in succession the added digital signal which indicates the self-correlation function of the detected signal obtained by addition into the specified address, making possible the updating.

8. A method of inspecting the internal pressure of a hermetically sealed container as claimed in claim 1, wherein the measured period obtaining process related to the self-correlation function of the detected signal includes a processing for issuing a gate open instruction signal when the content of the temporarily stored digital data signal indicated the self-correlation function reaches the zero cross level where it changes from positive to negative and issuing a gate close instruction signal when it reaches the zero cross level where the value returns to positive from negative and then changes again to negative from positive.

9. A method of inspecting the internal pressure of a hermetically sealed container as claimed in claim 1, wherein said analysis and arithmetic operation processings of the detected signal are performed in parallel together with processings for executing analog comparison and operation for the detected signal to a preset lower level, issuing a gate open instruction signal when it becomes lower than the lower level and making impossible the period measurement related to the self-correlation function of the detected signal.

10. A method of inspecting the internal pressure of a hermetically sealed container as claimed in claim 1, wherein the internal pressure adequacy discrimination and output processing includes a processing of executing digital comparison and operation between a counted value of clock pulses counted within the measured period obtained from the self-correlation function of the detected signal and present numbers of reference pulses.

11. A method of inspecting the internal pressure of a hermetically sealed container as claimed in claim 1, wherein said internal pressure adequacy discrimination and output processing includes a processing for issuing an abnormal condition detection signal for continuous fault discrimination exceeding a preset value.

12. An apparatus for inspecting the internal pressure of a hermetically sealed container, wherein an synthetic system circuit is composed of a hitting device which compulsorily excites vibration on the elastic wall of a hermetically sealed container, a vibration detecting device which converts vibration on the elastic wall into an electrical signal, a digital self-correlation function operation circuit for obtaining the self-correlation function of the detected signal, a period counter for measuring the period of self-correlation function, and a period discriminator which is capable of setting the discrimination value, being provided with a discrimination function for the counted value and comparing and discriminating said counter output.

13. An apparatus for inspecting the internal pressure of a hermetically sealed container as claimed in claim 12, wherein said hitting device and vibration detecting device are built into a pressure sensing head in the form of an integrated unit.

14. An apparatus for inspecting the internal pressure of a hermetically sealed container as claimed in claim 13, wherein the vibration detecting device is magnetically shielded from the hitting device.

15. An apparatus for inspecting the internal pressure of a hermetically sealed container as claimed in claim 14, wherein said vibration detecting device is concentrically surrounded at its circumference with a cylindrical shield made of ferro magnetic material.

16. An apparatus for inspecting the internal pressure of a hermetically sealed container as claimed in claim 15, wherein said cylindrical shield is provided with its lower open end in the incoming direction of the lines of magnetic force with its diameter reduced as compared to the upper end.

17. An apparatus for inspecting the internal pressure of a hermetically sealed container as claimed in claim 12, wherein said digital self-correlation function operation circuit allows an amplitude limiter to compress logarithmicly the amplitude of the detected signal to be prepared at its preceding stage.

18. An apparatus for inspecting the internal pressure of a hermetically sealed container as claimed in the claim 12, wherein said digital self-correlation function operation circuit is composed of an analog to digital converter which converts the detected signals one by one into digital code, a sub-memory which temporarily stores said digital signals in succession into the specified address making possible the renewal, a multiplication circuit which regularly multiplies according to the equation after sequentially reading out the relevant digital signal, an adder circuit for adding regularly said multiplied digital signals and a main memory which temporarily stores said added digital signals in succession into the specified address, making possible the renewal.

19. An apparatus for inspecting the internal pressure of a hermetically sealed container as claimed in claim 12, wherein said digital self-correlation function operation circuit is connected in parallel with a detected signal level discrimination circuit having a preset discrimination level.

20. An apparatus for inspecting the internal pressure of a hermetically sealed container as claimed in the claim 12, wherein the period discriminator is connected with an abnormal condition monitoring counter circuit consisting of a counter which counts a fault discrimination signal and is reset by a good discrimination signal, and a presettable counted value comparison and discrimination circuit.

21. An apparatus for inspecting the internal pressure of a hermetically sealed container as claimed in claim 12, wherein said synthetic system circuit comprises a timing control circuit which totally controls the hitting device, vibration detection device, digital self-correlation function operation circuit, period counter and period discriminator.

* * * * *